US00PP25720P3

(12) United States Plant Patent
Hammond

(10) Patent No.: US PP25,720 P3
(45) Date of Patent: Jul. 14, 2015

(54) *GAURA* PLANT NAMED 'GBAWH02-0'

(50) Latin Name: *Gaura lindheimeri*
Varietal Denomination: GBAWH02-0

(71) Applicant: Frank Hammond, Narre Warren East (AU)

(72) Inventor: Frank Hammond, Narre Warren East (AU)

( * ) Notice: Subject to any disclaimer, the term of this patent is extended or adjusted under 35 U.S.C. 154(b) by 145 days.

(21) Appl. No.: 13/815,551

(22) Filed: Mar. 7, 2013

(65) Prior Publication Data

US 2014/0259248 P1 Sep. 11, 2014

(51) Int. Cl.
*A01H 5/04* (2006.01)
*A01H 5/02* (2006.01)

(52) U.S. Cl.
USPC ..... Plt./432
CPC ..... *A01H 5/02* (2013.01)

(58) Field of Classification Search
USPC ..... Plt./432
See application file for complete search history.

*Primary Examiner* — Anne Grunberg
(74) *Attorney, Agent, or Firm* — Cassandra Bright

(57) ABSTRACT

A new and distinct *Gaura lindheimeri* cultivar named 'GBAWH02-0' is disclosed, characterized by exceptionally short plants of very compact habit, leaves with anthocyanin flushed foliage and stems, as well as short peduncles and white flowers. The new variety is a *Gaura*, and is normally used as an ornamental garden or container plant.

1 Drawing Sheet

Latin name of the genus and species: *Gaura lindheimeri*.
Variety denomination: 'GBAWH02-0'.

BACKGROUND OF THE INVENTION

The new cultivar is the product of chance discovery. The new variety originated as a naturally occurring whole plant mutation of *Gaura* 'GBAPI01-01', Ser. No. 13/815,548, filed concurrently to this application.

The new variety was discovered by the inventor, Frank Hammond, a citizen of Australia during November of 2007 at a research nursery in Victoria Australia. After identifying the new variety as a potentially interesting selection, the inventor continued confidential testing and propagation of 'GBAWH02-0' assessing stability of the unique characteristics of this variety.

Asexual reproduction of the new cultivar 'GBAWH02-0' was first performed in Victoria, Australia by vegetative cuttings in January of 2008. 'GBAWH02-0' has since produced more than 5 generations by vegetative cuttings and has shown that the unique features of this cultivar are stable and reproduced true to type.

SUMMARY OF THE INVENTION

The cultivar 'GBAWH02-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'GBAWH02-0'. These characteristics in combination distinguish 'GBAWH02-0' as a new and distinct *Gaura lindheimeri* cultivar:

1. Exceptionally short plants.
2. Very compact plant habit.

3. Stems and foliage flushed with anthocyanin coloration.
4. Short peduncles.
5. White flowers.

PARENT COMPARISON

Plants of the new cultivar 'GBAWH02-0' are similar to the parent, *Gaura lindheimeri* 'GBAPI01-0', in most horticultural characteristics. The new variety, however, produces white flowers compared to the dark pink flower of the parent, 'GBAPI01-0'.

COMMERCIAL COMPARISON

Plants of the new cultivar 'GBAWH02-0' are similar to plants of the commercial variety, *Gaura lindheimeri* 'My Melody' U.S. Plant Pat. No. 14,557, in most horticultural characteristics. However, plants of the new cultivar 'GBAWH02-0' produce flower buds colored near RHS Red-purple 58A, whereas this comparator produces flower buds colored near Yellow 4D and flushed with Red 39A and 39B. Plant stems of 'GBAWH02-0' are colored near Green 137D with faint flushing Red-Purple 59A: stems of 'My Melody' are Green 137C, without any flushing present. Foliage of 'GBAWH02-0' is colored near RHS Green 137A with strong flush Greyed-Purple N186C; 'My Melody' has foliage colored near Green 137C and 138A with a margin near Yellow-Green 144C, without any Greyed-Purple flushing. In addition plants of the new cultivar 'GBAWH02-0' are shorter than plants of the comparator 'My Melody', with typical plants of 'GBAWH02-0' reaching a height of approximately 22 cm in a pot, and plants of 'My Melody' reaching a height around 40 cm in a similar pot size.

BRIEF DESCRIPTION OF THE PHOTOGRAPH

The accompanying photograph in FIG. 1 illustrates in full color a typical plant of 'GBAWH02-0' grown in a greenhouse. The pot size is a commercial 6 inch pot. The plant shown is approximately 12 weeks old.

DETAILED BOTANICAL DESCRIPTION

In the following description, color references are made to The Royal Horticultural Society Colour Chart except where general terms of ordinary dictionary significance are used. The following observations and measurements describe 'GBAWH02-0' plants grown in a commercial controlled greenhouse in Oxnard, Calif. Temperatures ranged from 15° C. to 28° C. during the day and 18° C. to 22° C. at night. No artificial light, photoperiodic treatments or chemical treatments were given to the plants. Measurements and numerical values represent averages of typical plant types.

Botanical classification: *Gaura lindheimeri* 'GBAWH02-0'.

PROPAGATION

Time to initiate roots: 15 to 20 days at approximately 20° C.

Root description: Fibrous, colored near RHS Greyed-Orange 165D.

PLANT

Growth habit: Very compact, upright perennial.

Pot size of plant described: 6 inch.

Height: 22 cm.

Plant spread: 40 cm.

Growth rate: Rapid.

Branching characteristics: Basal branching, or nearly at soil level. No lateral produced above 1.5 cm above soil level.

Length of primary branches: Approximately 15 cm.

Diameter of branches: Approximately 0.35 cm.

Quantity of primary branches: Average 20.

Characteristics of primary lateral branches:

- *Form*.—Irregular round, some flat sides.
- *Color*.—Near RHS Green 137D with faint flushing Red-Purple 59A.
- *Texture*.—Scant pubescence.
- *Strength*.—Strong, somewhat flexible.

Internode length: Average 1.2 cm.

FOLIAGE

Leaf:

- *Arrangement*.—Alternate, simple.
- *Average length*.—5.8 cm.
- *Average width*.—1.3 cm.
- *Shape of blade*.—Elliptic.
- *Apex*.—Acute.
- *Base*.—Attenuate.
- *Margin*.—Nearly entire, infrequent shallow serrations present on some leaves.
- *Texture of top surface*.—Scant pubescence visible under magnification.
- *Texture of bottom surface*.—Glabrous.
- *Aspect*.—Flat to very slightly undulating.
- *Color*.—Young foliage upper side: Near RHS Green 137A with strong flush Greyed-Purple N186C. Young foliage under side: Near RHS Green 137A with strong flush Greyed-Purple N186C. Mature foliage upper side: Near RHS Green 137A. Mature foliage under side: Near RHS Green 137B.
- *Venation*.—Type: Pinnate. Venation color upper side: Near RHS Green 137C. Venation color under side: Near RHS Green 137D.
- *Petiole*.—Sessile.

FLOWER

Natural flowering season: Spring through Summer.

Inflorescence and flower type and habit: Single zygomorphic flowers produced on terminal and axillary racemes.

Persistent or self-cleaning: Self-Cleaning.

Bud:

- *Shape*.—Cylindric.
- *Length*.—1.4 cm.
- *Diameter*.—0.3 cm.
- *Color*.—Near RHS Red-Purple 58A.

Raceme:

- *Diameter*.—Average 6 cm.
- *Length*.—Average 8 cm.
- *Flowers per raceme*.—5 to 7.

Flower size:

- *Diameter*.—Average 3.1 cm.
- *Length*.—Average 2.0 cm.

Corolla/petals:

- *Quantity of petals*.—4.
- *Arrangement*.—Symmetrical whorl.
- *Petal length*.—1.5 cm.
- *Petal width*.—1.0 cm.
- *Corolla tube length*.—1.4 cm.
- *Corolla tube diameter*.—0.2 cm.
- *Texture*.—Glabrous.
- *Petal apex*.—Acute.
- *Petal base*.—Attenuate.
- *Petal shape*.—Spatulate.
- *Margin*.—Entire.
- *Aspect*.—Upwardly cupped.
- *Petal color*.—When opening: Upper surface: Near RHS White N155B. Lower surface: Near RHS White N155B. Fully opened: Upper surface: Near RHS White N155D. Lower surface: Near RHS White N155D.
- *Outer corolla tube color*.—Near RHS Red-Purple 58A with stripes of Green 137B.
- *Outer corolla tube color*.—Near RHS Yellow-Green N144B.

Calyx/sepals:

- *Quantity per flower*.—4.
- *Shape*.—Linear.
- *Length*.—1.5 cm.
- *Width*.—0.3 cm.
- *Apex*.—Acute.
- *Base*.—Truncate.
- *Margin*.—Entire.
- *Texture*.—Glabrous.
- *Aspect*.—Undulating and strongly reflexed back.
- *Color*.—Upper Surface: Near RHS White N155C with stripes of Red-Purple 58A and base faintly flushed Green 137B. Lower Surface: Near RHS White N155C with stripes of Red-Purple 58A and base faintly flushed Green 137B.

Peduncle:

- *Length*.—Average 5 cm.
- *Diameter*.—Approximately 0.2 cm.
- *Color*.—Near RHS Green 137A flushed with Greyed-Purple N186C.

*Orientation*.—Straight, approximately 15 degree angle from stem.
*Texture*.—Glabrous.
*Strength*.—Strong.

Pedicel: Not present, directly attached by corolla tube to Peduncle.

Fragrance: Very faint.

REPRODUCTIVE ORGANS

Stamens:
*Number*.—8.
*Filament length*.—Approximately 1.2 cm.

Anthers:
*Shape*.—Linear.
*Length*.—Approximately 0.25 cm.
*Color*.—Near RHS Red-Purple 58A.
*Pollen*.—Color: Near RHS Greyed-Yellow 162A. Quantity: Scant.

Pistil:
*Number*.—1.
*Length*.—2.5 cm.
*Style*.—Length: 1.5 cm. Color: Near RHS White N155C with upper portion Red-Purple 58A.
*Stigma*.—Shape: Bi lobed. Color: Near RHS Yellow-White 158B.
*Ovary*.—Ovary Color: Near RHS White 155C. Ovary Length: Approximately 1 cm. Ovary diameter: Approximately 0.1 cm. Ovary shape: Linear.

OTHER CHARACTERISTICS

Seeds and fruits: Not observed to date.

Disease/pest resistance: Neither resistance nor susceptibility to diseases or pests has been observed in this variety.

Temperature tolerance: The new variety tolerates temperatures from approximately −5° to 35-8° C.

What is claimed is:

1. A new and distinct cultivar of *Gaura* plant named 'GBAWH02-0' as herein illustrated and described.

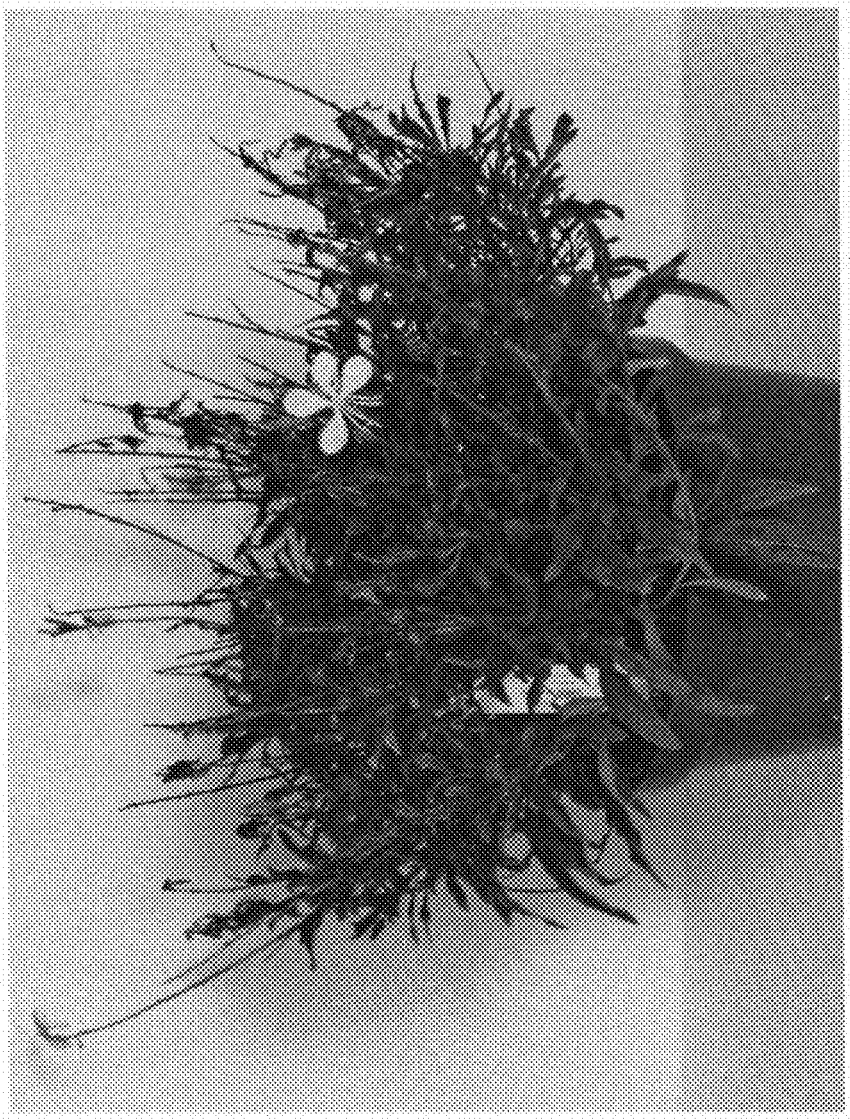

* * * * *